United States Patent
Kangasniemi et al.

(10) Patent No.: US 6,595,776 B2
(45) Date of Patent: Jul. 22, 2003

(54) APPLICATOR SYSTEM FOR DENTAL POSTS AND ANCHORS AND USE OF SAID APPLICATOR SYSTEM

(75) Inventors: Ilkka Kangasniemi, Turku (FI); Pekka Vallittu, Kuusisto (FI)

(73) Assignee: Stick Tech Oy, Turku (FI)

(*) Notice: Subject to any disclaimer, the term of this patent is extended or adjusted under 35 U.S.C. 154(b) by 0 days.

(21) Appl. No.: 09/900,878

(22) Filed: Jul. 10, 2001

(65) Prior Publication Data

US 2003/0013065 A1 Jan. 16, 2003

(51) Int. Cl.⁷ .............................. A61C 5/02
(52) U.S. Cl. .................. 433/81; 433/90; 433/224
(58) Field of Search .................. 433/81, 220, 221, 433/224, 89, 90

(56) References Cited

U.S. PATENT DOCUMENTS

| | | | |
|---|---|---|---|
| 4,472,141 A | 9/1984 | Dragan | 433/90 |
| 5,165,893 A * | 11/1992 | Thompson | 433/224 |
| 5,295,828 A * | 3/1994 | Grosrey | 433/81 |
| 5,445,523 A | 8/1995 | Fischer et al. | 433/90 |
| 5,464,348 A * | 11/1995 | Fischer et al. | 433/26 |
| 5,816,816 A * | 10/1998 | Scharf | 433/220 |
| 5,915,970 A * | 6/1999 | Sicurell, Jr. et al. | 433/220 |
| 5,919,044 A | 7/1999 | Sicurelli, Jr. et al. | 433/220 |
| 5,934,903 A * | 8/1999 | Marlin | 433/81 |
| 5,964,592 A | 10/1999 | Hites et al. | 433/221 |
| 6,183,253 B1 * | 2/2001 | Billet et al. | 433/81 |
| 6,386,865 B1 * | 5/2002 | Suh et al. | 433/27 |

FOREIGN PATENT DOCUMENTS

WO    WO 98/52486    11/1998

OTHER PUBLICATIONS

Vallittu, "Ultra–high Modulus Polyethylene Ribbon As Reinforcement for Denture Polymethacrylate: A Short Communication," 13 *Dent. Mater.* 381 (1997).

* cited by examiner

*Primary Examiner*—John J. Wilson
(74) *Attorney, Agent, or Firm*—James C. Lydon

(57) ABSTRACT

An applicator system (2) which includes a fiber-reinforced composite (FRC) post (4) or anchor in its non-polymerized form including a resinous matrix and fibers, i.e., a prepreg (4); and an applicator tube (8). The inner diameter ($d_T$) of the tube (8) is essentially the same or slightly larger than the outer diameter ($D_{P/A}$) of the FRC post (4) in its non-polymerized form. The outer diameter ($D_T$) end of the tube through which the FRC post is applied is essentially the same or slightly smaller that the coronal opening of the canal (6). The applicator system (2) may be used to prepare permanent or temporary root canal (6) posts, to make a tooth canal (6) filling and to make a post and/or anchorage system that forms a continuous FRC structure from the apex of the tooth to the coronal part of the tooth.

13 Claims, 1 Drawing Sheet

APPLICATOR SYSTEM FOR DENTAL POSTS AND ANCHORS AND USE OF SAID APPLICATOR SYSTEM

FIELD OF INVENTION

This invention relates to an applicator system for application of reinforced composite post or anchor into a dentinal canal. This invention further relates to the use of the system.

BACKGROUND OF THE INVENTION

The publications and other materials used herein to illuminate the background of the invention, and in particular, cases to provide additional details respecting the practice, are incorporated by reference.

Existing systems for anchorage of dental constructions such as crowns and large fillings to remaining roots are based on the use of dental posts mostly made of high rigidity materials like metal alloys, ceramics or to reduce the rigidity they can be made of finally polymerized fiber reinforced composite materials as disclosed e.g. by Hites & Hites (U.S. Pat. No. 5,964,592). Common characteristics of these posts are that they are in their final straight shape and that they are rigid. Occasionally they exhibit tapered or structured surfaces for mechanical retention for the composite luting cements. The earliest fiber reinforced composite (FRC) posts were made of carbon/graphite fibers with epoxy polymer matrix resulting in flexural modulus of 40 to 60 GPa. The most recent FRC posts are made of glass or silica fibers with a epoxy or dimethacrylate polymer matrix having flexural modulus between 28 to 40 GPa. Clinically the advantage of FRC posts has been that these do not cause fracturing of roots even if they have been used in short post lengths compared to the length of the clinical crown. On the other hand, the fracture incidence with metallic and ceramic posts has been high. The biggest disadvantages of finally polymerized FRC posts are the low bonding strength between the FRC post and the composite luting cement or composite core material, and the inability to flex along the curved root canal. All commercially available PRC posts require preparing the root canal to the standardized form of the FRC post. The preparation reduces the quantity of dentine and thus, reduces strength of the remaining root. These shortcomings cause frequent debonding of the FRC posts from the core and cement and hamper seriously the preparation of curved root canals. As a result of the present preparation techniques perforation of the tooth root and the periodontal ligament often occurs resulting in an elevated risk of infection of periodontal tissues. On the other hand, if there is need for long post lengths, which is the case when using metallic or ceramic posts to reduce the functional stress at the end point of the post, the root canal sealing has been shown to deteriorate considerably. This can cause an infection, e.g. periapical periodontitis. Therefore a post system with an improved bonding characteristic that can be placed in curved individually shaped root canals even with short post lengths would be a welcome improvement.

It is known that polyethylene fiber products are being marketed for making posts in situ as disclosed. The polyethylene fibers are inserted into the root with a special handheld instrument by pushing the fiber ribbon from the middle. The root canal is filled with a dual curing composite to wet the fibers and to bond the post to the tooth root surface. The potential advantages of this system are that there is no interface between the post polymer matrix surface and the cement since it is of the same material and that there is no need to prepare straight cavities for the posts. Disadvantages of polyethylene fiber post system are that wetting of the fibers by the polymer matrix and bonding of the fibers to the polymer matrix are inadequate (Vallittu, Ultra-high-modulus polyethylene ribbon as reinforcement for denture polymethyl methacrylate. Dent Mater 1997;13:381–382), the control of wetting the fibers inside the root is impossible and use of woven fibers results in less than optimal orientation of the fibers in the root.

The state of the art fiber reinforcement material in dentistry is preimpregnated unidirectional glass fiber material as disclosed e.g. by Sicurelli & Masyr (WO 98/52486). There are four such materials available commercially: Jeneric Pentron's Fibrekor®, Ivoclar-Vivadent's Vectris® Stick Tech's Stick® and everStick™. These differ from the other fiber materials in two respects: the bonding between the fiber surface and the polymer matrix is significantly higher than with polyethylene fibers and the wetting of the fibers with the polymer-matrix is complete. This results in flexural strengths of up to 1280 MPa as compared to 350 MPa of the best polyethylene product and in elastic modulus of up to 28 GPa as opposed to 3–5 GPa of polyethylene composites.

The disadvantage of unidirectional glass fibers is their poor controllability in the clinical handling process. Considering a root canal of dimensions approximately 2 mm opening diameter and 1 mm end diameter, 5–10 mm length and being of considerable curvature imposes various problems for the insertion of a unidirectional, non woven, glass fiber bundle of approximately 1000 to 6000 individual fibers, impregnated with a low viscosity monomer liquid. The fibers fray, bend and tangle with each other when one tries to push them inside the canal. Once spread, it is next to impossible to collect the fibers back into order and try again.

Very similar devices to posts are root canal anchors called root canal screws that are actually just very short posts. These are manufactured only in the form of a metallic screw of maximum length of approximately 10 mm and minimum of 3 mm. In fact the division between an anchor and a post is not clear. In both cases however the root canal is prepared with a separate straight drill to make a close fit cavity for the screw. On the other hand, the screws can also be placed into other dentinal cavities and canals, such as those prepared in a vital tooth. These vital tooth screws are called parapulpal posts and they are most often used to improve retention of fillings to remaining teeth.

The indication for an anchor is the need for added fixation of a partial crown or filling of large dimensions. Fillings are generally attached through mechanical or chemical retention or both. The strength of chemical retention depends on bonding surface area and roughness and the chemical nature of the bond. Mechanical retention depends solely on the shape and surface roughness of the cavity. One could say that the less of the tooth is left for mechanical or chemical bonding the more important it is to create increased retention of posts and anchors. In this sense a crown with very little tooth support left is an extreme case of a filling and is a clear indication for a root canal post. The other extreme is a one-wall filling that in practice usually does not need any additional retention from a post nor an anchor. With larger cavities involving 2 or 3 walls, larger than that are already considered crowns, the achievable retention is dramatically reduced and there is an increasing need to create more retention artificially.

OBJECT AND SUMMARY OF INVENTION

The object of the present invention is to provide an alternative and/or improved system for application of a reinforced composite post or anchor into a dentinal canal.

The present invention concerns an applicator system for application of a reinforced non-polymerized composite post or anchor into a dentinal canal. The applicator system comprises a fiber-reinforced composite (FRC) post or anchor in its non-polymerized form comprising a resinous matrix and fibers; and an applicator tube wherein the inner diameter $d_T$ of said tube is essentially the same or slightly larger than the outer diameter $D_{P/A}$ of said FRC post or anchor in its non-polymerized form, and the outer diameter $D_T$ of the end of said tube through which the FRC post or anchor is applied into the canal is essentially the same or slightly smaller than the coronal opening of the canal.

The present invention further concerns the use of the applicator system for preparing permanent or temporary root canal posts for fixation of artificial crowns and/or for the treatment of endodontic and/or periapical infections, for making a root canal filling and for making a post and/or anchorage system that forms a continuous FRC structure from the apex of the tooth to the coronal part of the tooth.

DETAILED DESCRIPTION OF THE INVENTION

Figure 1:
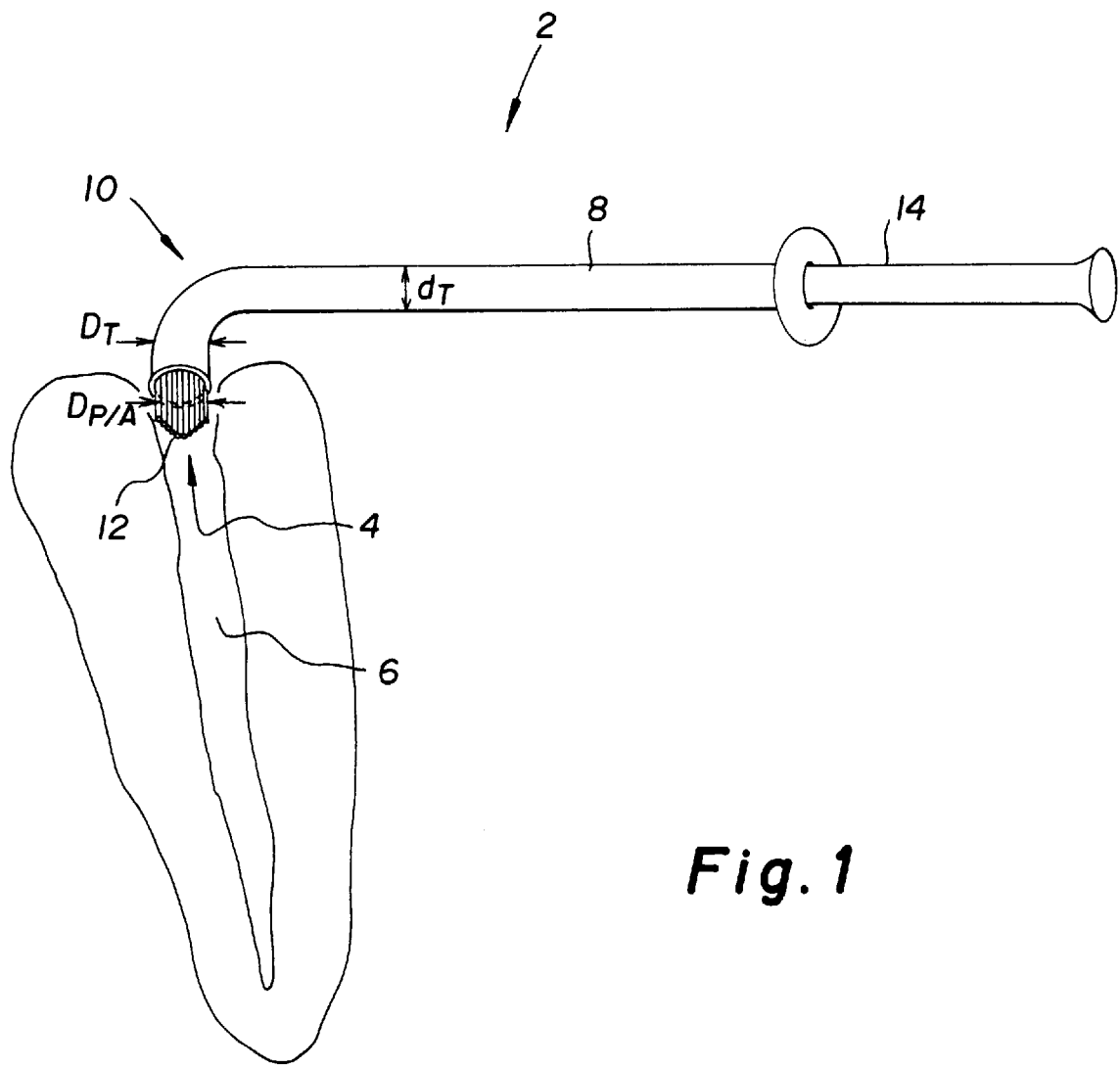
FIG. 1 shows the use of an applicator system according to the invention when applying a root canal post into the root canal.

The present invention describes an applicator system 2 for application of a fiber reinforced composite (FRC) post 4 or anchor into a dentinal canal. In this context the dentinal canal refers to a root canal 6 of a tooth or any canal of the tooth e.g. prepared for improving retention of fillings to remaining teeth by anchorage. The applicator system 2 comprises a FRC post 4 or anchor prepreg, i.e. a FRC post 4 or anchor in its non-polymerized form, and a tube 8 by which said prepreg can be pushed into a tooth canal 6. The prepreg comprises a resinous matrix and fibers. The resinous matrix may be composed of a monomer, a polymer or a polymer monomer mixture and optionally filler materials such as ceramic powder and/or opaquers, plasticizers etc. The fibers are preferably essentially continuous and/or essentially unidirectional. The fibers are preferably glass, silica, carbon graphite or polyethylene fibers.

The tube 8 may be stiff or flexible, transparent, opaque or partially opaque. The essential requirement is that the inner diameter $d_T$ of the tube is only slightly larger than the outer diameter $D_{P/A}$ of the FRC post or anchor, i.e. the diameter occupied by the volume of the fibers. If in such confinement a force is applied to one end of the fibers the entire length of the fiber bundle moves inside the tube 8 without being able to fray, bend or tangle. The end of the tube 8 is placed directly on or marginally inside a root canal 6 opening or the opening of a dentinal canal prepared to a vital tooth. The outer diameter $D_T$ of the tube 8 is essentially the same or slightly smaller than the coronal opening of the canal 6. Thus the canal 6 forms a continuation of the tube 8 thereby enabling trouble free transfer of the fibers into the canal 6. If nevertheless something goes wrong and the fibers are frayed, bent or tangled they can be pulled back into the tube 8 which forces the fibers in perfect order again.

The resinous matrix of the FRC post 4 or anchor can be polymerized by light initiation and/or by autopolymerization in the dentinal canal. If the tube 8 is transparent and flexible it is easy to check the wetting of the fibers. If the fibers are prewetted the tube 8 may also be opaque. In the latter case wetting can only be done using a light curing resin. The fibers of the FRC post 4 or anchor can comprise optical fibers allowing light polymerization of the resinous matrix in the dentinal canal.

Once the fibers are in place in the canal the outside portion of the fibers, i.e. the coronal part may be placed in any direction wished. This allows the dentist to direct the core part of the post or anchor in an optimal direction for building of the crown or filling. If the fibers are unidirectional this may be done without compromising the strength of the construction. Since the resinous matrix of the FRC post or anchor prepreg is polymerized in the root canal, with or without additional composite luting cement, the additional cements or dentine adhesives are chemically adhered to the FRC post or anchor during polymerization. After being polymerized in the root canal and twisted to the desired direction according to the angulation of the crown or filling to be made, the core particulate filler composite material is polymerized to the oxygen inhibition layer of the coronal part of the FRC post or anchor. This results in a durable bond between the core composite and PRC post or anchor. The fibers may be wetted at the factory with a light curing resin (prepreg) or at the dentist office using a dual curing resin. This is to say that embodiments according to the invention described above the fibers may or may not be preimpregnated with monomer resin.

For molar regions it may be preferential that the tube is temporarily or permanently shaped into an arch 10 as in FIG. 1 so as to be able to bring the tube to the canal opening from an optimal direction.

The end of the fiber bundle may be cut into a conical shape so that the tip 12 of the bundle is pointed or blunt but only a fraction of the main fiber bundle as shown in FIG. 1. This is to allow the shape of the fiber bundle to better fit to the shape of the root canal.

The insertion force may be applied to the end of the fibers by a separate piston 14 as in FIG. 1 well fitted to the diameter of the tube 8. Another way is to precure the rear end of the fiber bundle, through which the insertion force is applied, into the shape of a piston. Thus the fibers partially outside and partially inside the tube would be stiff whilst the other end of the fibers would be non-cured, elastic and maybe even non-impregnated with resin. However they may be preimpregnated with polymer or polymer-monomer gel according to earlier inventions disclosed by Vallittu et al. (WO 96/25911 and WO 99/45890) or with a monomer or any mixture containing monomer or polymer. Such mixtures could contain e.g. microfillers, opaquers or alike.

The tip of the FRC post prepreg could be polymerized into a shape that easily penetrates into the root canal and finally stops at the apex. The polymerized apical tip can additionally contain antimicrobial agents to heal the apical periodontal infections. The FRC post or anchor can be used as a temporary or permanent root canal filling material.

It will be appreciated that the system of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

What is claimed is:

1. An applicator system for application of a reinforced non-polymerized composite post or anchor into a dentinal canal comprising:

a) a fiber-reinforced composite post or anchor in its non-polymerized form comprising a resinous matrix and fibers having an outer diameter ($D_{F/A}$); and b) an applicator tube containing said post or anchor therein, wherein (i) an inner diameter ($d_T$) of said applicator tube is essentially the same or slightly larger than said outer diameter ($D_{P/A}$) of said post or anchor in its non-polymerized form, and (ii) an outer diameter ($D_T$) of said applicator tube through which the post or anchor is applied into said dentinal canal is essentially the same or slightly smaller than a coronal opening of said canal, wherein said fibers of said post or anchor comprise essentially continuous and essentially unidirectional fibers.

2. The applicator system of claim 1, wherein said fibers are selected from at least one member of the group consisting of glass fibers, silica fibers, carbon fibers, graphite fibers and polyethylene fibers.

3. The applicator system of claim 1, wherein said applicator tube is flexible.

4. The applicator system of claim 1, wherein said applicator tube is rigid.

5. The applicator system of claim 1, wherein said applicator tube is transparent.

6. The applicator system of claim 1, wherein said applicator tube is opaque.

7. The applicator system of claim 1, wherein said resinous matrix is polymerized by light initiation and/or by autopolymerization in said dentinal canal.

8. The applicator system of claim 1, wherein said fibers comprises optical fibers capable of allowing light polymerization of the resinous matrix in said dentinal canal.

9. The applicator system of claim 1, wherein an end of said post or anchor which is first applied into said dentinal canal is prepolymerized, is impregnated with antimicrobial agents, or both.

10. The applicator system of claim 1, wherein said resinous matrix in its non-polymerized form is a polymer, and said composite is wetted just prior to placement in said dentinal canal.

11. A method of making a tooth canal filling, comprising
   i) applying a reinforced non-polymerized composite post or anchor into a dentinal canal; and
   ii) polymerizing said composite post or anchor, wherein said post or anchor is applied by means of the applicator system of claim 1.

12. The method of claim 11, wherein said fiber reinforced composite comprises a post or anchor suitable for permanent or temporary fixation of an artificial crown and/or for the treatment of endodontic and/or periapical infections.

13. The method of claim 11, wherein said post or anchor forms a continuous fiber reinforced composite structure extending from an apex of a tooth to a coronal part of said tooth.

* * * * *